United States Patent
Knebel et al.

(10) Patent No.: US 10,495,865 B2
(45) Date of Patent: Dec. 3, 2019

(54) METHOD AND DEVICE FOR THE SPIM ANALYSIS OF A SAMPLE

(71) Applicant: LEICA MICROSYSTEMS CMS GMBH, Wetzlar (DE)

(72) Inventors: Werner Knebel, Kronau (DE); Frank Sieckmann, Eppingen (DE); Florian Fahrbach, Heidelberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 226 days.

(21) Appl. No.: 15/566,728

(22) PCT Filed: Apr. 18, 2016

(86) PCT No.: PCT/EP2016/058564
§ 371 (c)(1),
(2) Date: Jan. 22, 2018

(87) PCT Pub. No.: WO2016/166374
PCT Pub. Date: Oct. 20, 2016

(65) Prior Publication Data
US 2018/0149851 A1    May 31, 2018

(30) Foreign Application Priority Data
Apr. 17, 2015    (LU) .......................... 92695

(51) Int. Cl.
*G02B 21/18* (2006.01)
*G01N 21/47* (2006.01)
(Continued)

(52) U.S. Cl.
CPC ............. *G02B 21/18* (2013.01); *G01N 21/47* (2013.01); *G02B 21/0052* (2013.01);
(Continued)

(58) Field of Classification Search
CPC .. G02B 21/18; G02B 21/362; G02B 21/0064; G02B 21/0052; G02B 21/367; G02B 21/10; G02B 21/06; G01N 21/47
(Continued)

(56) References Cited

U.S. PATENT DOCUMENTS 3,877,788 A * 4/1975 Sprague ............. G01M 11/0228
356/124
8,792,162 B2 * 7/2014 Lippert ............... G02B 21/0032
359/385
(Continued)

FOREIGN PATENT DOCUMENTS

DE        10257423 A1    6/2004
DE    102004034957 A1    2/2006
(Continued)

*Primary Examiner* — Seung C Sohn
(74) *Attorney, Agent, or Firm* — Leydig, Voit & Mayer, Ltd.

(57) ABSTRACT

A method for single plane illumination microscopy (SPIM) analysis of a sample includes simultaneously illuminating multiple sample layers by a single sheet of light. Detection light emanating from the individual sample layers is detected at different times and/or at different positions in a detection beam path. The detection beam path is branched using beam splitters and an effective refractive power of the individual beam splitters is zero.

27 Claims, 16 Drawing Sheets

(51) Int. Cl.
*G02B 21/00* (2006.01)
*G02B 21/10* (2006.01)
*G02B 21/36* (2006.01)
*G02B 21/06* (2006.01)

(52) U.S. Cl.
CPC ......... *G02B 21/0064* (2013.01); *G02B 21/10* (2013.01); *G02B 21/362* (2013.01); *G02B 21/367* (2013.01); *G02B 21/06* (2013.01)

(58) Field of Classification Search
USPC ..................................................... 250/222.1
See application file for complete search history.

(56) References Cited

U.S. PATENT DOCUMENTS

| | | |
|---|---|---|
| 2006/0012866 A1 | 1/2006 | Wolleschensky |
| 2006/0033987 A1 | 2/2006 | Stelzer |
| 2016/0048014 A1 | 2/2016 | Knebel et al. |

FOREIGN PATENT DOCUMENTS

| | | |
|---|---|---|
| DE | 102010049751 A1 | 5/2012 |
| DE | 202011110077 U1 | 11/2012 |
| WO | WO 2013017855 A1 | 2/2013 |
| WO | WO 2014147261 A1 | 9/2014 |

\* cited by examiner

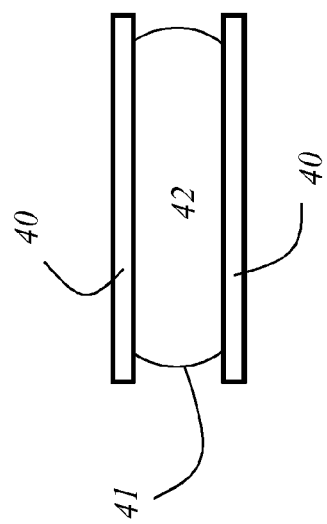
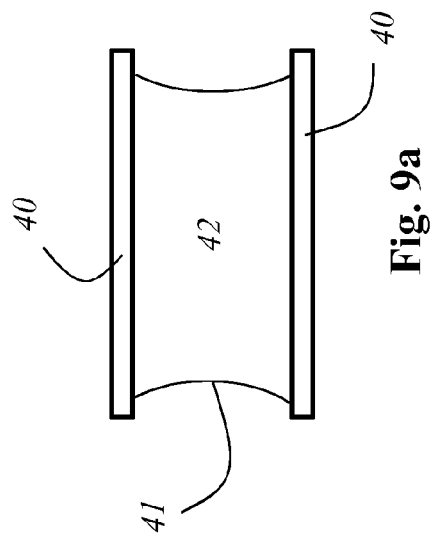

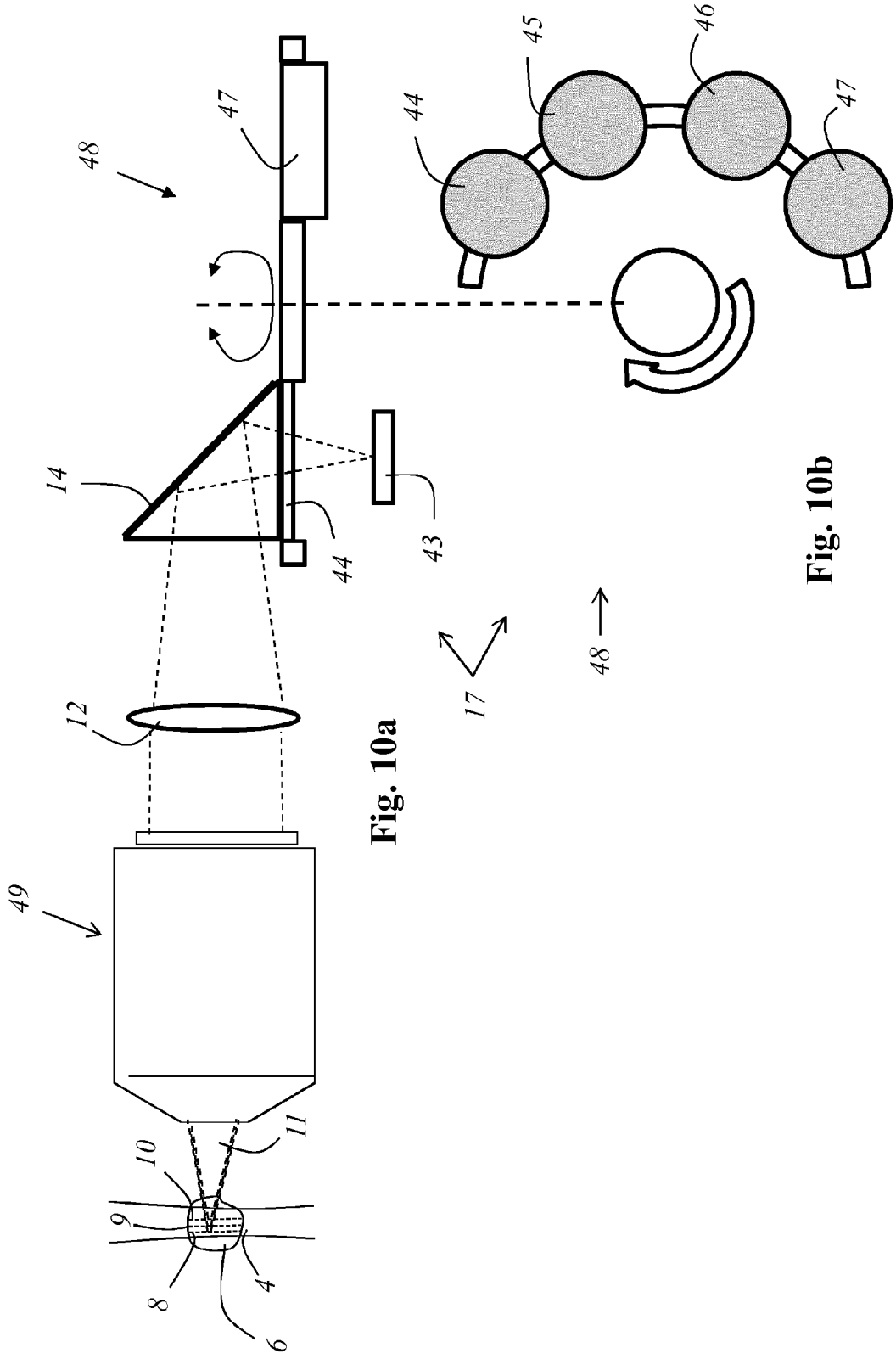

METHOD AND DEVICE FOR THE SPIM ANALYSIS OF A SAMPLE

CROSS-REFERENCE TO PRIOR APPLICATIONS

This application is a U.S. National Stage Application under 35 U.S.C. § 371 of International Application No. PCT/EP2016/058564 filed on Apr. 18, 2016, and claims benefit to Luxembourgian Patent Application No. LU 92695 filed on Apr. 17, 2015. The International Application was published in German on Oct. 20, 2016 as WO 2016/166374 A1 under PCT Article 21(2).

FIELD

The invention relates to a method for the SPIM analysis of a sample. Furthermore, the invention relates to a device for executing such a method and to a device for the SPIM analysis of a sample, said device having an illumination device for generating a sheet of light and a detection arrangement comprising a detection lens system and a detection beam path.

BACKGROUND

The SPIM technique (single plane illumination microscopy), in which illumination of the sample is carried out in layers, permits an acquisition of image data that is faster and gentler on the sample than point-by-point scanning of a sample, for example. A known application of SPIM technology is the field of fluorescence microscopy, in which fluorophores in the sample are excited by laser light. In the known SPIM technology, an excitation takes place in this case in a layer of a sample illuminated by an illumination light sheet (also termed a "light strip"). To generate a SPIM image, the sample is illuminated by the sheet of light, while the observation of the sample layer illuminated in this way takes place in a vertical direction by detection of the fluorescent or scattered light. From the successively obtained images of different sample layers, in particular from a stack of images of sample layers parallel to one another, a three-dimensional representation of the sample can be generated.

A microscope that works according to the SPIM method is described in DE 102 57 423 A1. With this microscope a sample is illuminated by a thin light strip, while the observation takes place perpendicular to the plane of the illuminating light strip. The illumination and the detection take place by way of two separate optical beam paths, each having separate optical systems, in particular having two separate lenses perpendicular to one another. The light strip is generated by an illumination lens and a cylindrical optical system upstream of this. To record the image, the sample is moved through the light strip, which is stationary relative to the detector, in order to record fluorescent and/or scattered light in layers using a two-dimensional detector. The layer image data obtained in this way can then be assembled into a dataset corresponding to a three-dimensional image of the sample.

An arrangement is disclosed in DE 10 2004 034 957 A1 for the microscopic observation of a sample via a microscope lens, in the housing of which, apart from the lens optical system, additional light guides are provided for the illumination light. The illumination light runs in this case initially parallel to the optical axis of the lens inside the light guides and then encounters an annular reflector having a small aperture mounted on the lens housing, which aperture focuses the illumination light with the aid of additional imaging elements perpendicular to the optical axis of the microscope lens and thus perpendicular to the observation direction into the sample. The illumination of the sample takes place two-dimensionally according to the SPIM principle here too. One problem in particular with this microscope is having to position the sample spatially inside the annular reflector.

An arrangement for illuminating a sample in SPIM microscopy is also disclosed in DE 20 2011 110 077 U1. The arrangement includes a light source for generating a light beam, means for generating a light strip from the light beam, and at least one lens, which has an optical system that is formed and intended to supply detection light emanating from the sample directly or indirectly to a detector. The arrangement also includes a deflection means downstream of the optical system of the lens for deflecting the light strip.

SUMMARY

In an embodiment, the present invention provides a method for single plane illumination microscopy (SPIM) analysis of a sample includes simultaneously illuminating multiple sample layers by a single sheet of light. Detection light emanating from the individual sample layers is detected at different times and/or at different positions in a detection beam path. The detection beam path is branched using beam splitters and an effective refractive power of the individual beam splitters is zero.

BRIEF DESCRIPTION OF THE DRAWINGS

The subject matter of the invention is shown by way of example and schematically in the drawings and is described below with reference to the drawings, wherein identical elements or elements having the same effect are mostly provided with the same reference signs. In particular, the influence of the different refractive indices of the materials through which the beams of rays pass was not taken into account for the most part when drawing in the beams of rays for the sake of clarity. The convergence angle of the beams of rays drawn in is thus frequently represented as identical for various materials or optical components in the drawings for simplification. The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIGS. 9a and 9b show the mode of operation of the infinitely adjustable adjusting elements;

FIGS. 10a and 10b show an eighth embodiment of a device according to the invention;

DETAILED DESCRIPTION

Figure 1:
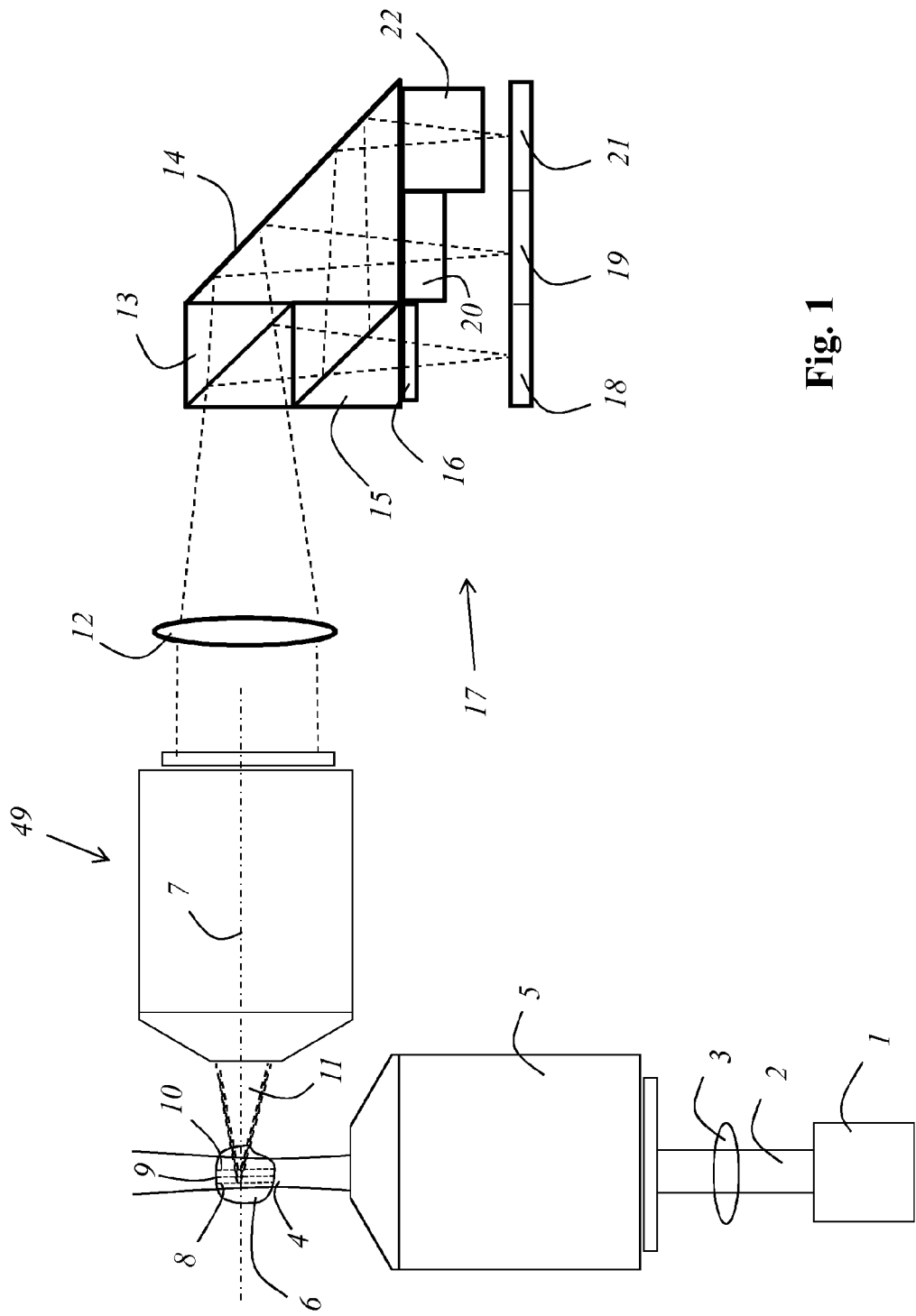
FIG. 1 shows a first embodiment of a device according to the invention with a branched detection beam path and surface detector elements, which are parts of the same surface detector.

An aspect of the present invention specifies a method that permits analysis of a sample in three dimensions that is even faster and/or gentler on the sample.

This is achieved according to an embodiment by a method in which multiple sample layers are simultaneously illuminated by a single sheet of light and in which the detection light emanating from the individual sample layers is detected at different times and/or at different positions.

Another aspect of the present invention specifies a device that permits analysis of a sample in three dimensions that is even faster and/or gentler on the sample.

This is achieved according to an embodiment by a device of the type mentioned at the outset, which is characterized in that the illumination device simultaneously illuminates multiple sample layers of a sample to be analyzed with the light sheet, and the detection arrangement detects the detection light emanating from the individual sample layers at different times and/or at different positions.

An embodiment of the invention has the very particular advantage that due to the simultaneous illumination of multiple sample layers, image data of these sample layers can be obtained very quickly, simultaneously or sequentially, in particular without the sample having to be moved relative to the detection arrangement. It is made possible in this way to record an image stack, which permits a three-dimensional reconstruction of the sample, quickly and gently with regard to the sample.

A more gentle analysis of a sample in three dimensions is facilitated in particular because the loading by the illumination light can be reduced on account of the faster acquisition of image data and because, as explained in detail further below, the sample does not have to be moved relative to the detection arrangement.

As is explained in detail further below, illumination of multiple sample layers can take place in a particularly advantageous manner with a single sheet of light, the spatial thickness of which is greater than the depth of field of the detection arrangement, so that the detection light emanating in each case, simultaneously or sequentially, from the sample layers simultaneously illuminated by one and the same sheet of light can be detected separately from one another.

In a particular embodiment of the method according to the invention, it is provided that the detection light emanating from the different sample layers is focused spatially separated, in particular simultaneously, on separate surface detector elements. Alternatively or in addition, it can also be provided that the detection light of the different sample layers is detected, in particular simultaneously, using a plurality of separate surface detector elements. Such an embodiment makes it possible in a particularly advantageous manner to be able to record image data from multiple different sample layers at the same time.

It can be provided particularly advantageously in this case that the detection beam path is branched and has a plurality of detection beam path branches, each having at least one surface detector element. The branching of the detection beam path can be achieved in particular with the aid of beam splitters, which can be formed, for example, as beam splitter cubes and/or as neutral beam splitters.

In a particularly advantageous manner, the optical path lengths of the detection beam path branches (each measured from the detection lens to the respective surface detector element) are adjusted for imaging the multiple illuminated sample layers using an adjusting device in such a way that the detection light emanating from a sample layer is focused onto a first surface detector element of a first detection beam path branch, and the detection light emanating from another sample layer is focused onto a second surface detector element of a second detector beam path branch. A third and further detection beam path branches can naturally also be present, wherein the detection light of a third and further sample layers is focused correspondingly onto the surface detector elements of these detection beam path branches.

It can be achieved in this way that a dedicated surface detector element is associated with each of the sample layers illuminated, wherein the detection light emanating from a sample layer in each case is focused onto the associated surface detector element. In particular, if the branching of the detection beam path is realized by neutral beam splitters, detection light of another sample layer naturally also reaches a surface detector element not associated with it; however, this detection light is not focused onto this surface detector element, so that during the acquisition of image data using this surface detector element it only contributes to background noise. However, this background noise can at least be reduced subsequently in the processing of the image signals and/or image data obtained. It has proved to be the case that the described effect plays at most a subordinate role in practice anyway.

It is also possible that the detection light is split into different detection beam path branches as a function of at least one detection light property. For example, the detection light property can comprise the spatial orientation of a linear polarization and/or the association with a predetermined or predeterminable wavelength range. It is possible, for example, that the branching of the detection beam path is brought about by color beam splitters. It can be achieved in this way that with regard to each sample layer only the detection light of a certain wavelength or of a certain wavelength range is detected.

The adjusting device enables the optical path lengths of the detection beam path branches to be adapted sample-specifically in such a way that, for each of the sample layers, a surface detector element is located in an optically corresponding plane. Or expressed another way: the optical light paths of the detection beam path branches can be adjusted in such a way that each of the surface detector elements "watches" its own sample layer. Such an adaptability of the optical path lengths has the particular advantage that the different formation of different samples, especially with regard to extent and/or refractive index, can be taken into account. In particular it can be taken into account whether the detection light has to cover a longer or a shorter path through the sample before it exits the sample. Moreover, an adaption of the optical path lengths can also be undertaken precisely, for example, when exchanging optical components in the detection beam path, such as when changing the detection lens system, for example.

With regard to this in particular, it can advantageously be provided that the optical path lengths of the individual detection beam path branches are adjusted independently of one another and/or can be adjusted independently of one another. It is made possible in this way to be able to associate a certain sample layer individually with each surface detector element in an optically corresponding plane. The user has the particular advantage in this respect of being able to adapt flexibly to the sample occurrences and in particular of analyzing precisely the sample layers that are relevant to him.

To this end in particular, the adjusting device can comprise a plurality of adjusting elements, wherein each detection beam path branch can have its own adjusting element, with which the optical path length of the respective detection beam path branch is adjusted and/or can be adjusted.

The detection beam path branches can, especially in the region from the detection lens to a beam splitter, overlap in part and moreover, especially in the region from a beam splitter to the respective surface detector element, run spatially separated from one another.

To be able to adjust the optical path lengths of the individual detection beam path branches independently of one another and individually, it is advantageous if each detection beam path branch has its own adjusting element for adjusting the optical path length in the region in which it does not overlap with any other detection beam path. Alternatively or in addition, however, it is also possible for a common adjusting element to be present in the region in which two or more detection beam path branches overlap, which element acts on a plurality of detection beam path branches and with which the optical path lengths of a plurality of detection beam path branches are variable at the same time.

In another type of embodiment of the method according to the invention, which in particular does not require any branched detection beam path, the detection light emanating from the different sample layers is focused in temporal succession onto the same surface detector element.

This can be realized, for example, in that the detection light emanating from one of the sample layers and passing through a detection lens is guided on a detection beam path of which the optical path length is adjusted by means of an adjusting device in such a way that the detection light emanating from this sample layer is focused onto the surface detector element, wherein the surface detector element for obtaining image data of this sample layer is read with this setting of the path length, and that following this in time the optical path length of the detection beam path is adjusted by means of the adjusting device in such a way that the detection light emanating from another of the sample layers is focused onto the surface detector element, wherein to obtain image data of the other sample layer with the other setting of the optical path length, the surface detector element is read again. In this way the multiple sample layers, which can be arranged in particular perpendicular to the optical axis of the detection lens and parallel to one another, can be imaged successively one after another onto the surface detector element and image data can be obtained which is specific to each sample layer.

Regardless of whether the detection of the detection light now takes place simultaneously or sequentially and regardless of whether the detection of the detection light of the individual sample layers takes place via a branched detection beam path or an unbranched detection beam path, the sample layers to be analyzed can advantageously be aligned parallel to one another. A procedure of this kind has the particular advantage that a simple arrangement of the surface detector element (in the case of an unbranched detection beam path) or the surface detector elements (in the case of a branched detection beam path) is facilitated. In particular, it is not necessary to rotate a surface element and/or to provide any optical adaption elements to be able to take account of different orientations of the individual sample layers, even if this were possible, however.

It is particularly advantageous, especially with respect to fast and effective detection, if a stack of a multiplicity of sample layers aligned parallel to one another is illuminated and imaged simultaneously or sequentially.

It is particularly advantageous if the sample layers are oriented perpendicular to the optical axis of the detection lens, because the detection light emanating from different positions of the respective sample layer then has to cover roughly the same light path through the sample.

In a particular embodiment, the sample layers to be analyzed are spaced at a distance from one another that is greater than the optical resolution of the detection arrangement used.

The sheet of light for the simultaneous illumination of the multiple sample layers can be formed, for example, with the aid of a cylindrical optical system from an illumination light beam, in particular a laser illumination light beam.

Alternatively, however, a quasi light sheet can also be generated by waving an illumination light beam, which is in particular circular in cross section, back and forth in a light sheet plane. For example, it can be provided that initially, for example using a laser light source, an illumination light beam that is round in cross section is generated, which can be waved quickly back and forth by a beam deflection device that is adjustable in respect of the deflection angle and can in particular be the scanner of a scanning microscope, in such a way that this forms a quasi light sheet. In particular, it can be provided that the illumination light beam is waved quickly back and forth in such a way that the surface detector element receiving the detection light generates the same detection signals, at least to a large extent, as for illumination using a sheet of light that was formed using a cylindrical optical system, and/or that the quasi light sheet for the detector used is not to be distinguished from a sheet of light generated using a cylindrical optical system, for example.

It can be provided in an advantageous manner that the light sheet plane is oriented perpendicular to the optical axis of the detection lens and/or that the light sheet can be deflected in such a way that it encounters the sample and/or runs through the sample at an angle different from zero degrees to the optical axis of the detection lens. An orientation of the light sheet plane perpendicular to the optical axis of the detection lens has the particular advantage that the sample layers can be illuminated in such a way that the light paths of the detection light up to exiting from the sample are identical, at least largely, relative to each detection layer.

In particular, if the sheet of light has an extension in the direction of the optical axis of the detection lens that is greater than the depth of field range of the detection arrangement, which comprises at least the detection lens and the detection beam path, it is possible to illuminate multiple sample layers simultaneously and to be able to detect the detection light emanating from the sample layers simultaneously or sequentially without having to move the sample.

After the detection light emanating from the multiple sample layers has been detected and image data taken in respect of each desired sample layer, other sample layers can be illuminated simultaneously with the sheet of light in a next step and the detection light emanating from the other different sample layers can be detected as described above. In this respect, it is possible to be able to analyze successively a tuple of n sample layers respectively and to use the image data obtained of all tuples for a 3D reconstruction of the sample, for example. This is regardless of whether the detection light emanating from the respectively simultaneously illuminated sample layers is detected in a branched detection beam path or in an unbranched detection beam path and regardless of whether the detection of the detection light emanating from the different sample layers takes place simultaneously or sequentially.

In order to illuminate multiple other sample layers with the sheet of light after multiple sample layers were already analyzed previously, the sample can be moved relative to the sheet of light, for example. Such a procedure has the advantage that the overall optical structure in respect of illumination and detection can remain unchanged, at least to a large extent. It may only be necessary to adapt the optical length of the detection beam path somewhat if the path length of the detection light through the sample up to exiting the sample changes.

However, such a procedure has the disadvantage that the sample could be damaged by movement of the sample. Movement of the sample can also be problematic if instruments, such as microelectrodes or microneedles, for example, project into the sample during the analysis. In such a case in particular, it is also possible to keep the sample stationary and instead to move the illuminating sheet of light relative to the sample. Moreover, the adjusting device can then be used to adapt the optical path length of the detection beam path and/or the individual detection beam path branches in such a way that focusing of the detection light emanating from the individual other sample layers onto the surface detector element or the surface detector elements is ensured.

In one embodiment that manages with especially few detector components, the surface detector elements are parts of the same surface detector, which can be formed, for example, as a CCD detector or as a CMOS detector or as an sCMOS detector. In particular, it can be provided in this case that the surface detector has a sensor surface, wherein different spatial portions of the sensor surface form the different surface detector elements. Such an embodiment is suitable in particular in a simultaneous detection of the detection light emanating from the multiple illuminated sample layers. In particular, by reading out the entire surface detector all information on all sample layers can be obtained simultaneously.

Alternatively, it is also possible that the surface detector elements are separate surface detectors or at least parts of surface detectors separate from one another. Such an embodiment has the advantage that the individual surface detector elements can be operated and read completely independently of one another.

The adjusting device for adjusting the optical path length of the detection beam path or for adjusting the optical path lengths of the detection beam path branches can be realized in an entirely different manner.

For example, it can be provided that the adjusting device or an adjusting element of the adjusting device has a plurality of different, transparent optical components, such as a plurality of glass blocks of different lengths, for example, which are insertable in exchange for one another into the detection beam path or into a detection beam path branch. By exchanging such an optical component for a longer optical component or a component having a higher refractive index, an extension of the optical path length can be achieved, while by exchanging such an optical component for another optical component that is formed shorter and/or has a lower refractive index, a reduction in the optical path length of the detection beam path or the detection beam path branch can be achieved.

In this context, reference is to be made to the fact that here and in the following, the material glass (for example in "glass block") is only mentioned by way of example. In general, any materials and material combinations that have the required optical properties for realizing the invention can be used for the optical components of the adjusting device and also for all the other optical components used. In particular, large parts of the optical components used and shown in the drawings (including the optical components of the adjusting device) can even consist in part or entirely of air and/or other gases or gas mixtures or even of liquids (such as water, oil, for example). For example, the mirrors used can be manifested as reflection prisms or alternatively also only as a simple standalone mirror surface. The beam splitters used can be simple beam splitter plates or also beam splitter cubes, for example.

It can be provided in particular that the adjusting device has a plurality of transparent optical components, which are insertable independently of one another into the detection beam path and/or into a detection beam path branch. For example, it is possible to insert a plurality of optical components spatially one behind another into the detection beam path or a detection beam path branch, wherein an extension of the optical path length is achievable by adding another optical component, while a shortening of the optical path length can be effected by removing one of the optical components.

In a particularly advantageous embodiment, which permits a rapid adjustment of the respective optical path length and ensures that the optical components are always optimally adjusted, the adjusting device or at least one adjusting element of the adjusting device has a plurality of optical components arranged on a turret or on a displacement arrangement. This makes it possible, for example by simple rotation of the turret, to exchange one optical component in the detection beam path or in a detection beam path branch for another optical component. It is also possible to exchange the optical components of a plurality of detection beam path branches simultaneously by a single rotation process or by a single displacement process, which facilitates a rapid and efficient adaption of the optical path lengths of a plurality of detection beam path branches in one adjustment step.

Alternatively or in addition, it can be provided generally that the adjusting device or an adjusting element of the adjusting device has at least one transparent block, for example a glass block, which is arranged movably, in particular rotatably and/or displaceably, in such a way that the proportion of the block located in the detection beam path and/or in a detection beam path branch is variable.

Alternatively or in addition, it can furthermore be provided quite generally that at least one of the surface detector elements is positioned along the optical axis thereof standing perpendicular to it independently of the other surface detector elements in such a way that the desired optical path length is achieved. In this case the surface detector element could either be anchored fixedly in its focus position or otherwise be held movably in the sense that its position along the optical axis can be adjusted, for example by means of a mechanical, pneumatic or electrical drive, or by a drive based on the piezoelectric effect, in order to reach a certain position on the optical axis. This drive can be part of the adjusting device. Such an adjustment could be carried out automatically or even manually between or also during individual measurements or image recordings.

In a particularly advantageous embodiment, which also permits in particular a continuous adjustment of the optical path length of the detection beam path or of one detection beam path or a plurality of detection beam path branches, the adjusting device or an adjusting element of the adjusting device has at least one optical component that is adjustable in geometrical and/or optical thickness.

For example, the adjusting device or an adjusting element of the adjusting device can have at least one optical component that is variable in its shape. This adjustable optical component can be realized in particular in that it has a fluid, in particular a liquid, arranged in a container, wherein the shape of the container is variable. In this way the geometrical length of the part of the optical component through which the detection light radiates can be changed. This can be achieved, for example, by directly changing the shape of the vessel. However, it is also possible to change the shape of the optical component by exerting a pressure on the fluid or by generating a vacuum.

For example, the adjustable optical component can have two transparent limiting discs, between which a fluid, in particular liquid, optical medium is arranged. By varying the spacing of the limiting discs, the geometrical thickness and thus also the optical thickness of the adjustable optical component can be varied. The transparent limiting discs can, for example, form a receiving space for the optical medium together with a flexible resilient, in particular tubular, film. The limiting discs can be pressed apart by pressurizing the fluid and thus the optical path length can be increased. By reducing the pressure acting on the fluid, the limiting discs can be moved towards one another and a reduction in the optical path length achieved thereby.

To avoid disruptive multiple reflections between the interfaces of the beam splitters and/or the optical components, it can advantageously be provided that at least one of the interfaces, in particular all the interfaces located in the detection beam path, is arranged at an angle different from 90 degrees to the incident direction of the detection light and/or that at least one of the interfaces, in particular all the interfaces located in the detection beam path, are arranged at an angle different from 90 degrees to the optical axis.

Filters, for example bandpass filters, can advantageously be applied to, in particular sputtered onto, the interfaces of the beam splitters and/or the optical components. This is to realize wavelength-specific detection, for example, and/or to block out light of the excitation wavelength.

In a particularly advantageous embodiment, at least one of the beam splitters and/or at least one of the optical components is configured so that aberrations are avoided or at least reduced and/or aberrations are at least compensated for.

To this end, at least one of the beam splitters and/or at least one of the optical components can have at least one curved interface, in particular an aspherically curved interface. Alternatively or in addition, it is also possible, for example, that at least one of the beam splitters or one of the optical components has an inhomogeneous refractive index across its cross section and thus develops a lens effect (GRIN lens). Alternatively or in addition, it is also possible for said purpose that at least one of the beam splitters and/or at least one of the optical components has a diffractive structure.

The effective refractive power of the beam splitters and/or of the optical components can amount to zero in a manner that is simple to realize, which as much as signifies that the focal length of these elements lies in infinity. An effective refractive power of zero ultimately also means that the convergence angle of the detection light beam focused in each case on a surface detector element by the respective beam splitter and the respective optical component is not changed. In the simplest case, an effective refractive power of the element of zero is achieved in elements consisting of a single material in that the front and the rear interfaces are flat.

However, it is advantageously also possible to use a beam splitter and/or an optical component having curved interfaces, wherein a refractive power of zero can nevertheless be achieved in that the curvature of its front interface and of its rear interface are identical. It is also possible in this regard to achieve an axial offset of the focus of the detection light with such a beam splitter and/or such an optical component; this is without the convergence angle of the respective detection light beam focused on a surface detector element changing, unlike the case of a lens.

The interfaces of identical curvature do not necessarily have to be the interfaces of the same beam splitter and/or optical component to achieve the described effect. On the contrary, it can also be provided advantageously that the first interface of the first beam splitter, for example, which the detection light encounters and the last interface for the individual detection beam path branches respectively are correspondingly identically curved. For the case that the refractive indices of said elements are different, however, at least one radius of curvature must be adapted accordingly to achieve the same effect.

Even in the case of an adjustable optical component, a particular additional axial offset of the focus of the detection light can be achieved. This is possible here too without the convergence angle of the respective detection light beam focused on a surface detector element changing, unlike the case of a lens.

For example, the adjustable optical component can have two transparent, curved limiting discs, between which a fluid, in particular a liquid, optical medium is arranged. By varying the spacing of the limiting discs, the geometrical thickness and thus also the optical thickness of the adjustable optical component can be varied. The transparent, curved limiting discs can, for example, form a receiving space for the optical medium together with a flexible resilient, in particular tubular, film. The limiting discs can be pressed apart by pressurizing the medium and thus the optical path length can be increased. By reducing the pressure acting on the medium, the limiting discs can be moved towards one another and a reduction in the optical path length can be achieved thereby. The two limiting discs are preferably curved in the same direction and have the same radius of curvature. Moreover, regardless of the curvature of the limiting discs, it can advantageously be provided that the refractive index of the fluid medium is adapted to the refractive index of the limiting discs. In particular, it can be provided that the refractive index of the medium is the same as that of the limiting discs.

The device according to the invention can advantageously include a scanning microscope or a confocal scanning microscope and/or be formed from a scanning microscope and/or a confocal scanning microscope. In this case, the beam deflection device of the scanning microscope or confocal scanning microscope, which device is adjustable in particular in respect of the deflection angle, can be used to generate a quasi light sheet as described above.

FIG. 1 shows schematically a first embodiment of a device according to the invention. The device has a light source 1, which can be formed, for example, as a laser and which generates a light beam 2. The light beam 2 is formed with the aid of a cylindrical optical system 3 into a sheet of light 4, which is focused using an illumination lens 5 onto a sample 6.

With regard to the drawing, the light sheet plane is perpendicular to the drawing plane. The light sheet plane is arranged perpendicular to the optical axis 7 of a detection lens 49. The sheet of light 4 illuminates multiple sample layers 8, 9, 10 simultaneously. The detection light 11 emanating from the individual sample layers 8, 9, 10 is collimated by the detection lens 49 and focused by a tube lens 12 and then passes to a first beam splitter 13, which reflects ⅔ of the detection light and transmits ⅓ of the detection light.

The reflected portion of the detection light 11 passes to a further beam splitter 15, which transmits half of the incident light and reflects the other half.

After passing a first optical component 16, which is part of an adjusting device 17 for adjusting the optical path lengths of the detection beam path branches, the portion of the detection light 11 reflected by the first beam splitter 13 and transmitted by the second beam splitter 15 reaches a first surface detector element 18. The optical path length of this detection beam path branch, at the end of which the first surface detector element is located, is adjusted so that the first surface detector element 18 is located in a plane corresponding optically to the first sample layer 8.

The portion of the detection light 11 transmitted through the first beam splitter 13 reaches a mirror 14 and is deflected by this to a second surface detector element 19, which the transmitted portion of the detection light 11 reaches after passing a second optical component 20, which is likewise part of the adjusting device 17. The second surface detector element 19 is arranged in a plane corresponding optically to the second sample layer 9. The detection light reflected by the second beam splitter 15 likewise encounters the mirror 14 and is deflected by this to a third surface detector element 21, wherein it passes a third optical component 22, which is likewise part of the adjusting device 17. The third surface detector element 21 is located in a plane corresponding optically to the third sample layer 10.

With the aid of the device, the detection light 11 of the different sample layers 8, 9, 10 can be detected, in particular simultaneously, by the separate surface detector elements 18, 19, 21. The surface detector elements 18, 19, 21 are parts of the same surface detector.

The device has the particular advantage that image data from three sample layers 8, 9, 10 can be recorded simultaneously. However, there is no restriction in this case to just three sample layers. On the contrary, even a substantially higher number of sample layers can be illuminated simultaneously in practice and the detection light emanating from these sample layers can be detected, in particular simultaneously.

After the image data with regard to the illuminated sample layers 8, 9, 10 has been obtained, further sample layers can be illuminated simultaneously, for example by moving the sheet of light 4 in the direction of the optical axis of the detection lens 49, and the detection light emanating from these further sample layers can be detected. In this case an adaption of the optical path lengths of the detection beam path branches is necessary at most.

Alternatively, an implementation without a first optical component 16 is also conceivable. The adjustment of the optical path lengths then takes place solely via the second optical component 20 and the third optical component 22.

Figure 2:
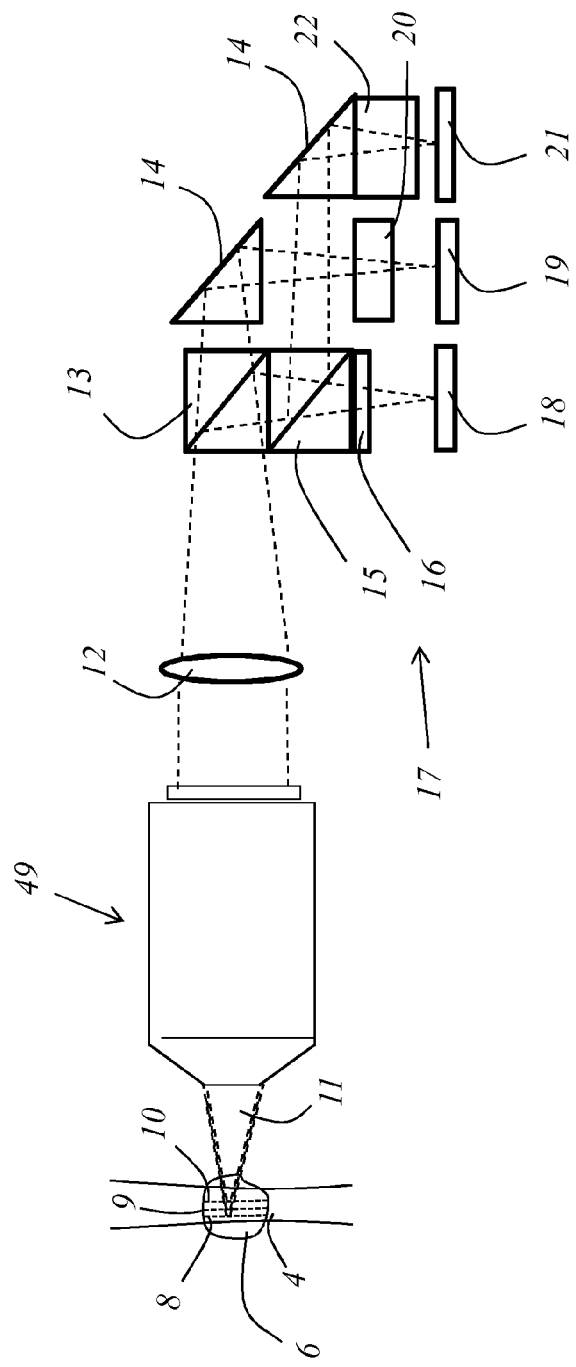
FIG. 2 shows a second embodiment of a device according to the invention with a branched detection beam path and surface detectors separate from one another.

FIG. 2 shows a second embodiment of a device according to the invention, which is constructed in a similar manner to the device shown in FIG. 1.

In this embodiment, the first surface detector element 18 and the second surface detector element 19 and the third surface detector element 21 are not constituents of one and the same surface detector, but are formed as separate surface detectors respectively. These can be three CCD cameras, for example.

Figure 3:
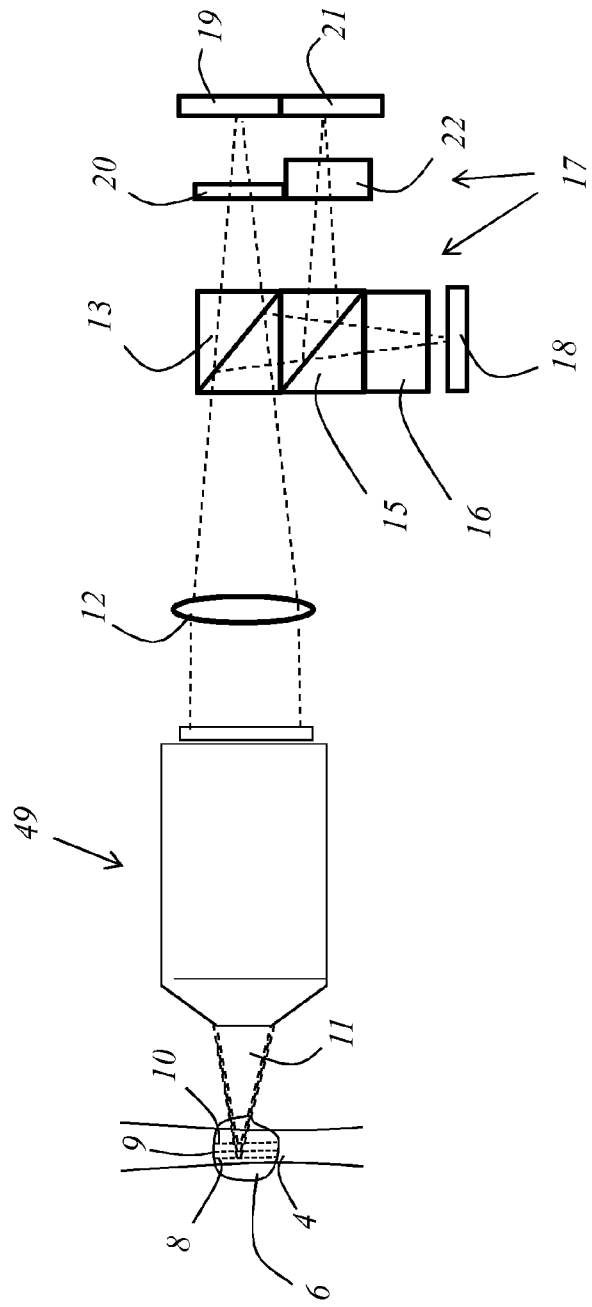
FIG. 3 shows a third embodiment of a device according to the invention.

FIG. 3 shows schematically a third embodiment of a device according to the invention, in which the detection light 11 focused by the tube lens 12 is split by a first beam splitter 13, which transmits ⅓ of the detection light and reflects ⅔.

The reflected portion of the detection light 11 reaches a second beam splitter 15, which reflects and transmits in the ratio 50:50. After passing a first optical component 16 for adaption of the optical path length, the portion of the detection light 11 transmitted by the second beam splitter 15 reaches a first surface detector 18.

The detection light 11 transmitted by the first beam splitter 13 passes, after passing a second optical component 20 without further deflection, directly to the second surface detector element 19, while the detection light 11 reflected by the second beam splitter 15, after passing a third optical component 22, reaches a third surface detector element 21. In this device too, the surface detector elements 18, 19, 21 are located in planes that are optically corresponding planes to the planes in which the sample layers 8, 9, 10 are located.

Figure 4:
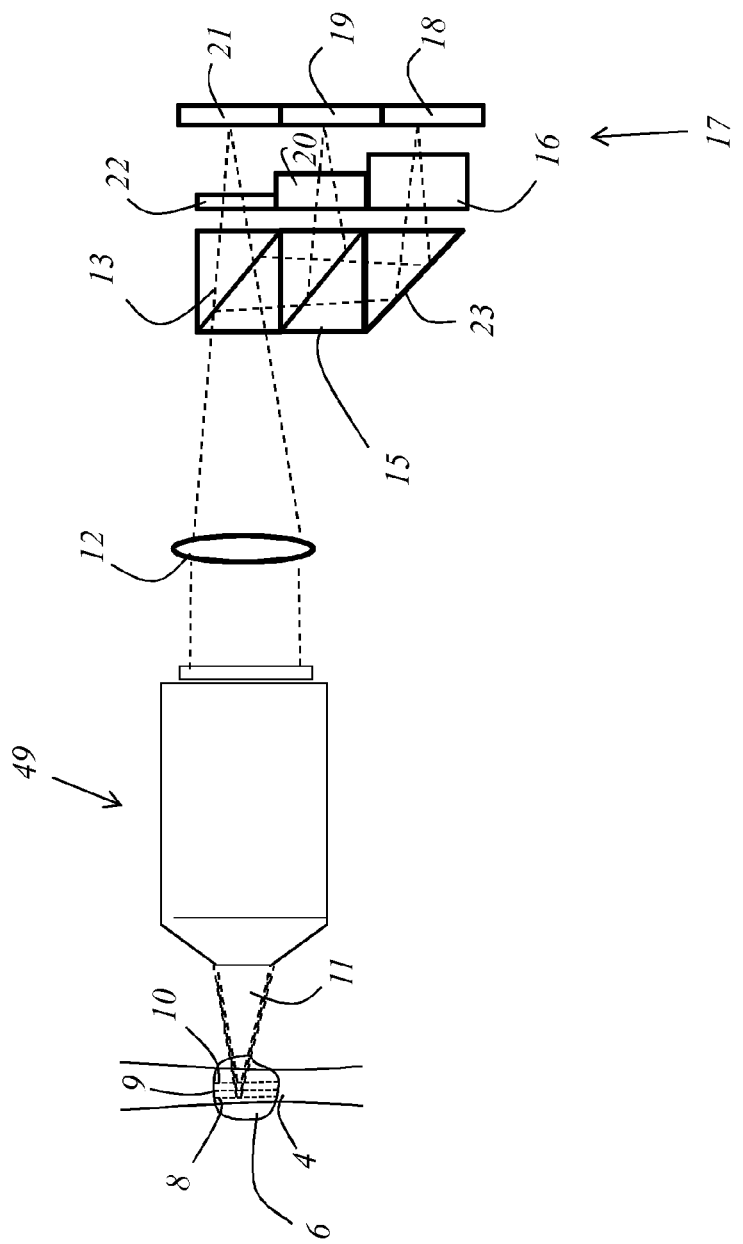
FIG. 4 shows a fourth embodiment of a device according to the invention.

FIG. 4 shows a fourth embodiment of a device according to the invention, in which the detection light 11 focused by the tube lens 12 is split by a first beam splitter 13, which transmits ⅓ of the detection light and reflects ⅔.

The reflected portion of the detection light 11 passes to a second beam splitter 15, which reflects and transmits in the ratio 50:50. The portion of the detection light 11 transmitted by the second beam splitter 15 is deflected by a deflection mirror 23 before it reaches the first surface detector element 18 after passing a first optical component 16, which is used to adjust the optical path length of the detection beam path branch.

After passing a third optical component 22 without further deflection, the detection light 11 transmitted by the first beam splitter 13 reaches the third surface detector element 21 directly, while the detection light 11 reflected by the second beam splitter 15 reaches a second surface detector element 19 after passing a second optical component 20. In this device too, the surface detector elements 18, 19, 21 are located in planes that are optically corresponding planes to the planes in which the sample layers 8, 9, 10 are located.

Figure 5:
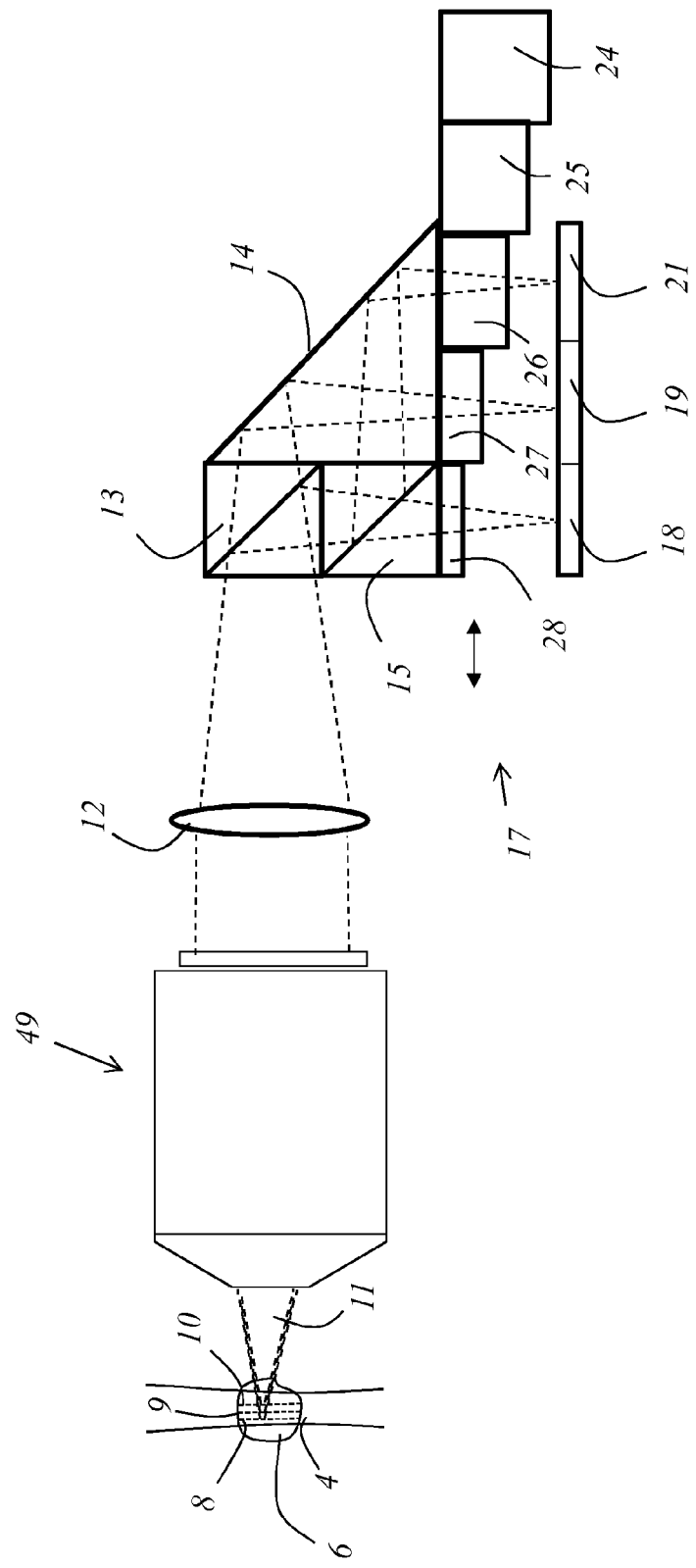
FIG. 5 shows a fifth embodiment of a device according to the invention having a special adjusting device in a first setting.

FIG. 5 shows schematically a fifth embodiment of a device according to the invention, which substantially corresponds in construction to the device shown in FIG. 1. The adjusting device 17 contains five glass blocks 24, 25, 26, 27, 28, which can be guided and moved together by means of a displacement device and of which—depending on the respective displacement position—a glass block 24, 25, 26, 27, 28 is arranged in one of the detection beam path branches respectively.

Figure 6:
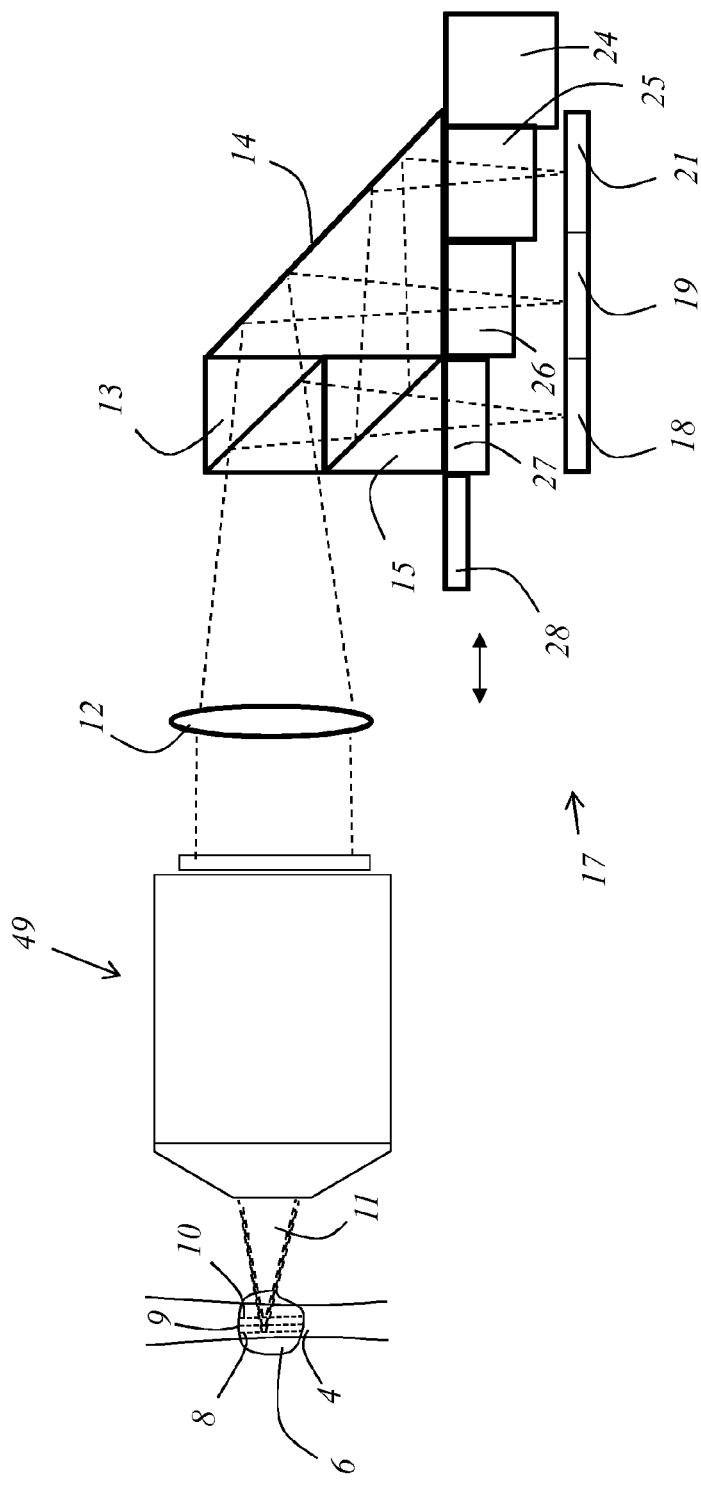
FIG. 6 shows the fifth embodiment with another setting of the adjusting device.

Starting out from the setting shown in FIG. 5, an extension of the optical path lengths of all the detection beam path branches can be achieved simultaneously by displacement of the glass blocks 24, 25, 26, 27, 28 to the left, as shown in FIG. 6.

Figure 7:
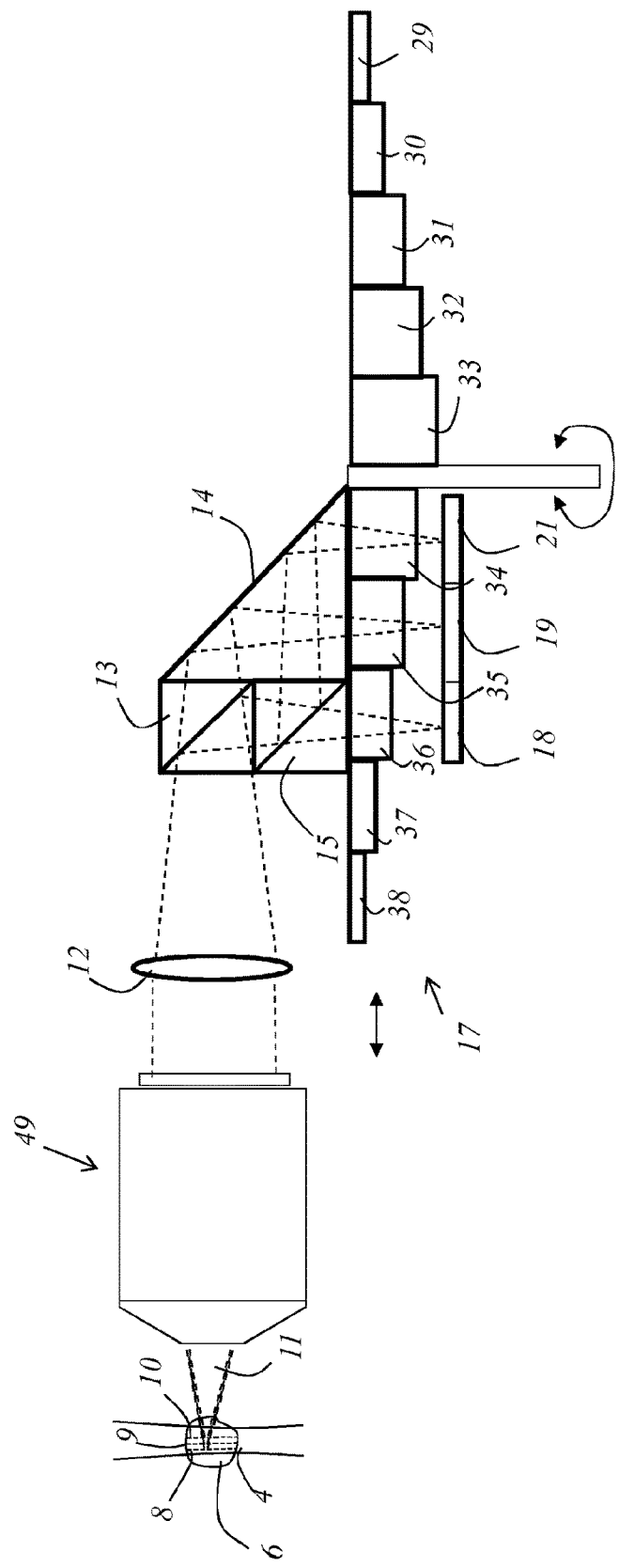
FIG. 7 shows a sixth embodiment of a device according to the invention.

Alternatively or in addition to a displacement device as shown in FIGS. 5 and 6, a rotating device can also be present as a constituent of the adjusting device 17, which can contain a multiplicity of glass blocks 29, 30, 31, 32, 33, 34, 35, 36, 37, 38 of different lengths, so that by changing the rotary position, different glass blocks 29, 30, 31, 32, 33, 34, 35, 36, 37, 38 can be positioned in the detection beam path branches in order to adapt the optical path lengths of the detection beam path branches, which is realized in the embodiment shown in FIG. 7.

Figure 8:
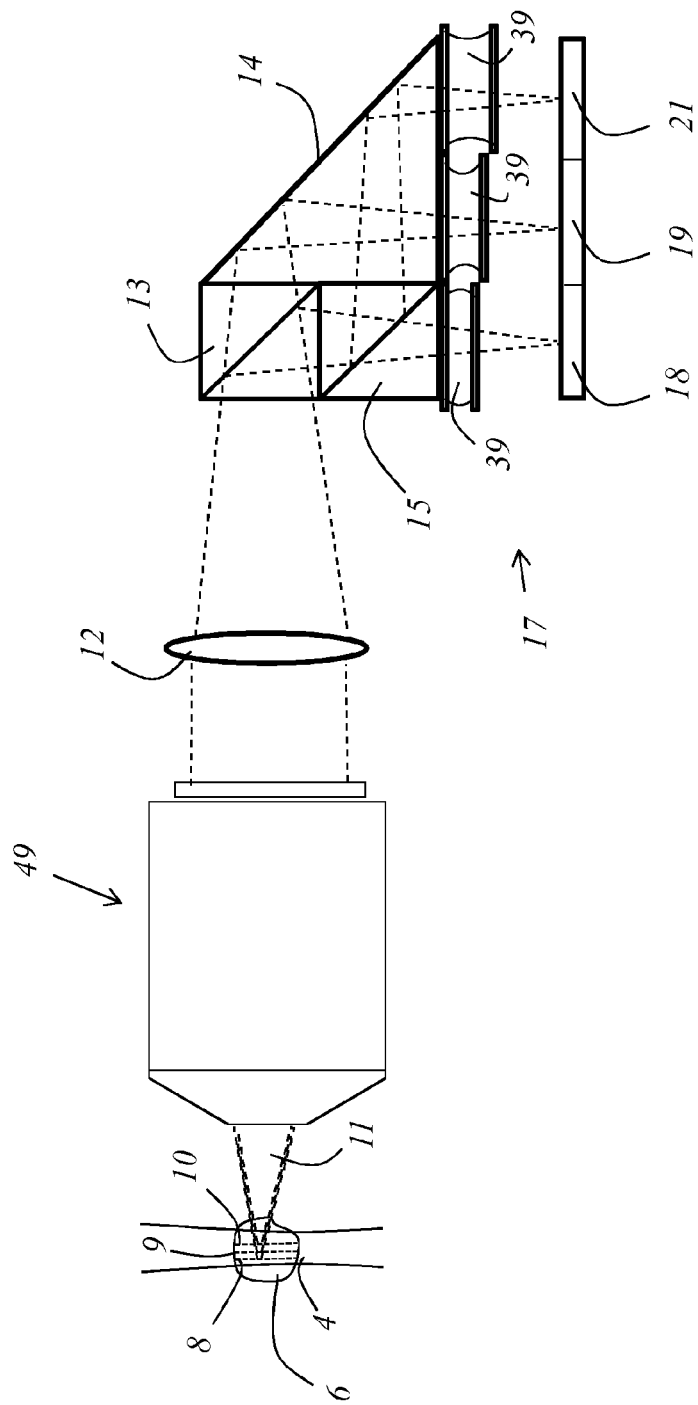
FIG. 8 shows a seventh embodiment of a device according to the invention having infinitely adjustable adjusting elements.

FIG. 8 shows a particular embodiment that largely corresponds in its basic structure to the embodiment according to FIG. 1.

However, an infinitely adjustable optical component 39 is arranged in each of the detection beam path branches. The infinitely adjustable optical components 39 can be adjusted independently of one another, so that the optical path lengths of the individual detection beam path branches can also be adjusted independently of one another.

The mode of operation of the infinitely adjustable optical components 39 is shown in greater detail in FIGS. 9a and 9b. Each of the infinitely adjustable optical components 39 has two transparent limiting discs 40, which together with an annular, resilient film 41 form a receiving space for a fluid 42. The spacing of the transparent limiting discs 40 can be varied, for example by varying the pressure on the fluid 42. It is also possible alternatively or in addition to adjust the spacing of the transparent limiting discs 40 directly, for example by means of a servomotor.

FIG. 10a shows an eighth embodiment of a device according to the invention with an unbranched detection beam path.

In this device, the detection light 11 emanating from the different sample layers 8, 9, 10 is focused not simultaneously, but sequentially onto a surface detector element 43. Specifically, the detection light 11 collimated by the detection lens 49 is bundled by a tube lens 12 and then deflected by a deflection mirror 14, so that after passing an optical component, namely a glass block 44, of an adjusting device 17, which contains a turret 48 having a plurality of glass blocks 44, 45, 46, 47 of different lengths, it reaches the surface detector element 43. The surface detector element 43 is located in an optical plane corresponding to a first sample layer 8.

Following the read-out of the optical surface detector element 43, the adjusting device 17 is rotated, so that another of the glass blocks 44, 45, 46, 47 enters the detection beam path, which is dimensioned so that now the surface detector element 43 is arranged in a plane corresponding optically to the second sample layer 9.

Following the detection of the detection light 11 emanating from the second sample layer 9, the turret 48 is rotated afresh and another of the glass blocks 44, 45, 46, 47 is thereby inserted into the detection beam path, in such a manner that the surface detector element 43 is now arranged in a plane that corresponds optically to the plane of the third sample layer 10.

Figure 11:
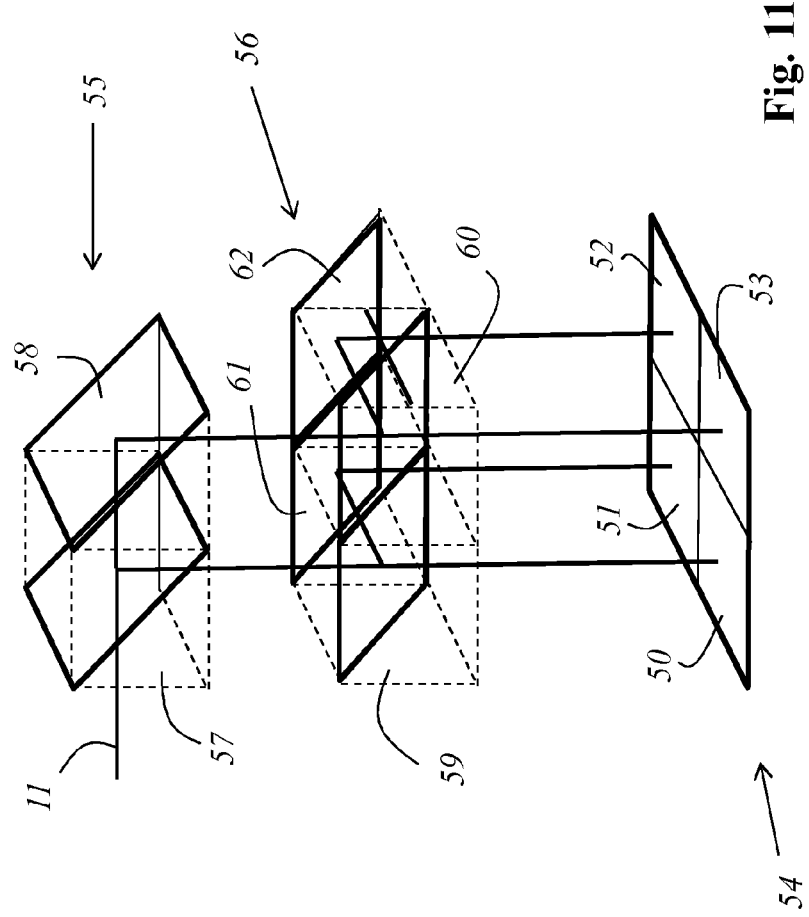
FIG. 11 shows an embodiment of a multidimensionally branched detection beam path.

FIG. 11 shows an embodiment of a multidimensionally branched detection beam path, in which a plurality of surface detector elements 50, 51, 52, 53 of a surface detector 54 are associated respectively with one of four sample layers. For greater clarity, the adjusting elements for adaption of the path lengths of the detection beam path branches are not shown in this drawing.

The multidimensional branching is achieved in that the detection light 11 is initially split spatially in a first splitter stage 55 by a first beam splitter 57, wherein the transmitted portion of the detection light 11 is deflected by a first deflection mirror 58.

A further splitting then takes place in a second splitter stage 56 of both the transmitted portion of the detection light 11 and of the reflected portion, wherein the second beam splitters 59, 60 and the second deflection mirrors 61, 62 of the second splitter stage 56 are oriented rotated by 90 degrees with regard to the respective optical axis and relative to the first beam splitter 57 and the first deflection mirror 58.

The embodiments that are shown in FIGS. 1 to 16b have interfaces that are aligned perpendicular to the input direction of the incident light and/or are plane-parallel to one another. However, this does not have to be realized in this manner.

For example, to avoid disruptive multiple reflections between the interfaces of the beam splitters 13, 15, 57, 59, 60 and/or the optical components 16, 20, 22, 24 to 38, it can be advantageously provided that at least one of the interfaces is arranged at an angle different from 90 degrees to the incidence direction of the detection light and/or that at least one of the interfaces, in particular all the interfaces located in the detection beam path, are arranged at an angle different from 90 degrees to the optical axis. Alternatively or in addition, it can be advantageously provided in particular that along the detection beam path at least interfaces directly following one another are not aligned parallel to one another.

Figure 12:
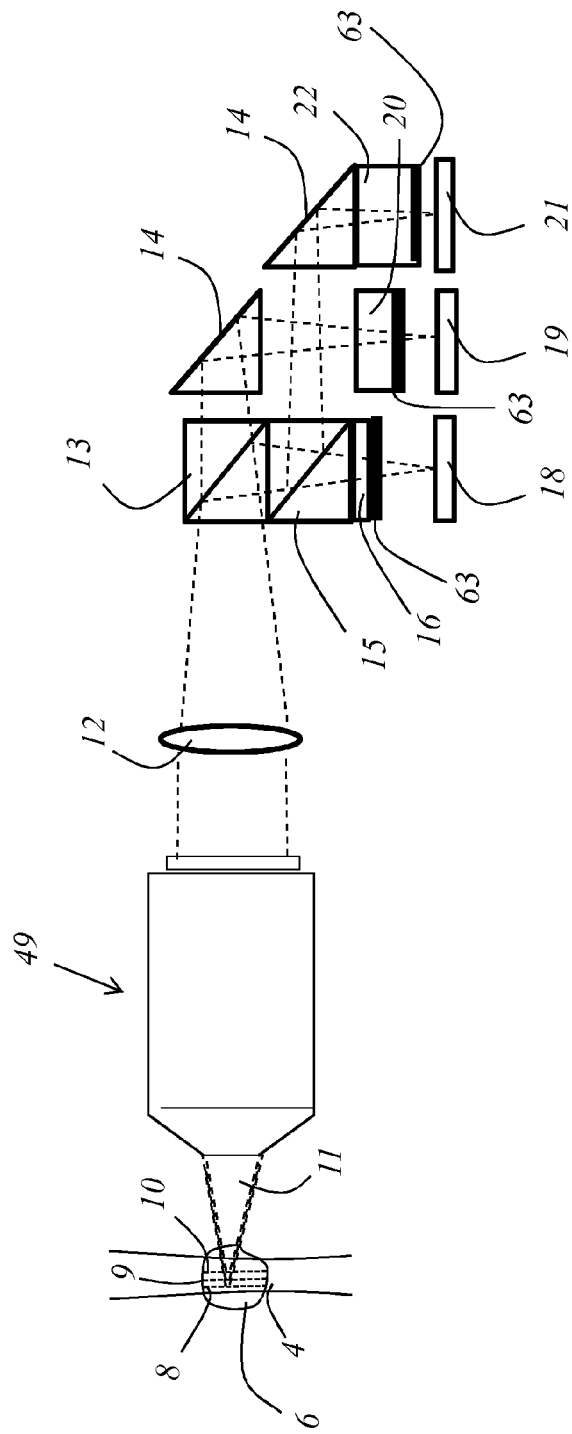
FIG. 12 shows a ninth embodiment of a device according to the invention having bandpass filters.

Furthermore, a filter, in particular a bandpass filter, can be applied, in particular sputtered onto, at least one of the interfaces. FIG. 12 shows an embodiment that corresponds substantially to the embodiment according to FIG. 2, wherein by way of example a bandpass filter 63 is applied, however, to the first optical component 16, the second optical component 20 and the third optical component 22. These bandpass filters 63 can be used for wavelength-specific detection, for example, and in particular for suppressing the light of an excitation wavelength of the light sheet 4.

The bandpass filters 63 can be formed in the same manner. However, it is also possible that the bandpass filters 63 are formed differently in respect of the wavelength range of the transmitted light, in order to be able to detect light of different wavelength ranges with the surface detector elements 18, 19, 21, for example. It is also possible to apply the bandpass filters 63 to the respective other interface of the first optical component 16, the second optical component 20 and the third optical component 22. Alternatively, the bandpass filters could also be arranged in another place on one of the beam splitters 13, 15, 57, 59, 60 and/or one of the optical components 16, 20, 22, 24 to 38 in the non-overlapping parts of the detection beam path branches.

It should be pointed out, moreover, that the beam splitters 13, 15, 57, 59, 60 and/or the optical components 16, 20, 22, 24 to 38 do not have to be manufactured from the same material, but can be. In particular, different materials can also be used advantageously. Even if adjoining elements are manufactured from the same material, these elements do not necessarily have to be manufactured together in one piece. However, this is entirely possible and particularly advantageous in some applications.

In a particularly advantageous manner, at least one of the beam splitters 13, 15, 57, 59, 60 and/or at least one of the optical components 16, 20, 22, 24 to 38 can be configured so that aberrations are avoided or at least reduced, and/or compensated for. To this end, at least one of the beam splitters 13, 15, 57, 59, 60 and/or at least one of the optical components 16, 20, 22, 24 to 38 can have at least one curved interface, for example, in particular an aspherically curved interface. Alternatively or in addition, it is also possible, for example, that at least one of the beam splitters 13, 15, 57, 59, 60 and/or at least one optical component 16, 20, 22, 24 to 38 has an inhomogeneous refractive index across its cross section (and thus develops a lens effect (GRIN lens)) and/or is composed of a plurality of elements with different optical properties.

Alternatively or in addition, it is also possible for said purpose that at least one of the beam splitters 13, 15, 57, 59, 60 and/or at least one of the optical components 16, 20, 22, 24 to 38 has a diffractive structure.

The embodiments shown in FIGS. 1 to 12 and 16a, 16b have beam splitters 13, 15, 57, 59, 60 and optical components 16, 20, 22, 24 to 38, the effective refractive power of which is equal to zero; or expressed another way, the focal length of these elements lies in infinity. An effective refractive power of zero ultimately means that the convergence angle ß of the respective detection light beam focused on a surface detector element through the respective beam splitter 13, 15, 57, 59, 60 and the respective optical component 16, 20, 22, 24 to 38 is not changed. In the simplest case, an effective refractive power of the element of zero in the case of elements consisting of a single material is achieved in that the front and rear interfaces are flat.

Figure 13:
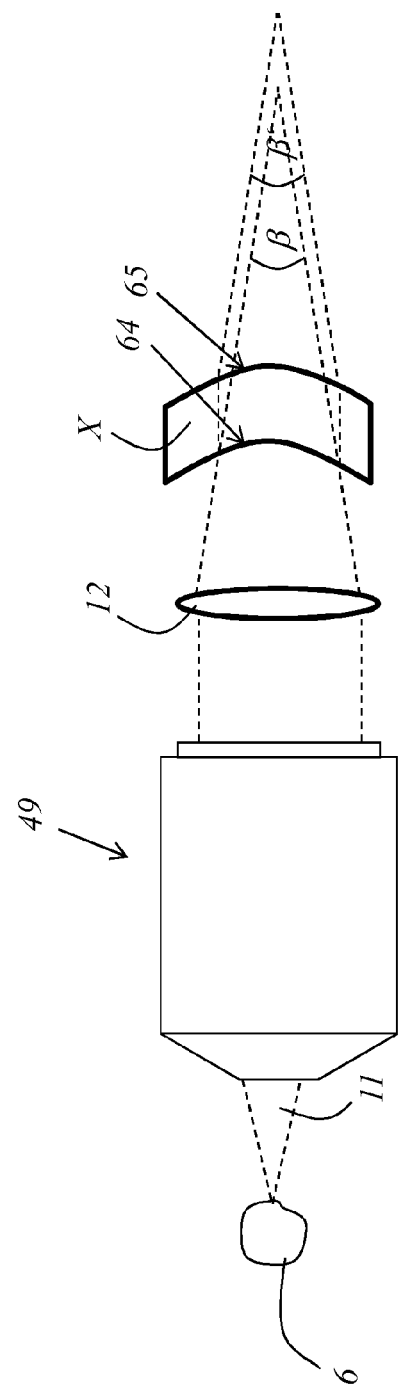
FIG. 13 is a schematic representation of the operating principle when using curved interfaces.

However, it is advantageously also possible to use a beam splitter 13, 15, 57, 59, 60 and/or an optical component 16, 20, 22, 24 to 38 (generally symbolized in FIG. 13 by the optical system X), the interfaces of which are curved, wherein nevertheless a refractive power of zero can be achieved in that the curvatures of the front interface 64 and the rear interface 65 are the same, as shown schematically and by way of example in FIG. 13. In this regard, it is also possible using such a beam splitter 13, 15, 57, 59, 60 and/or an optical component 16, 20, 22, 24 to 38 to achieve an axial offset of the focus of the detection light 11, as shown schematically in FIG. 13. This is without—differently than in the case of a lens—the convergence angle ß of the respective detection light beam focused on a surface detector element changing. Consequently the following applies: ß=ß'.

To achieve the effect described, the interfaces of identical curvature do not necessarily have to be the interfaces of the same beam splitter 13, 15, 57, 59, 60 and/or optical component 16, 20, 22, 24 to 38. On the contrary, it can advantageously also be provided that the first interface 66 of the first beam splitter 13, for example, which the detection light 11 encounters, and the last interface 67, 68, 69 respectively for the individual detection beam path branches are correspondingly identically curved (provided that they have the same refractive index).

Figure 14:
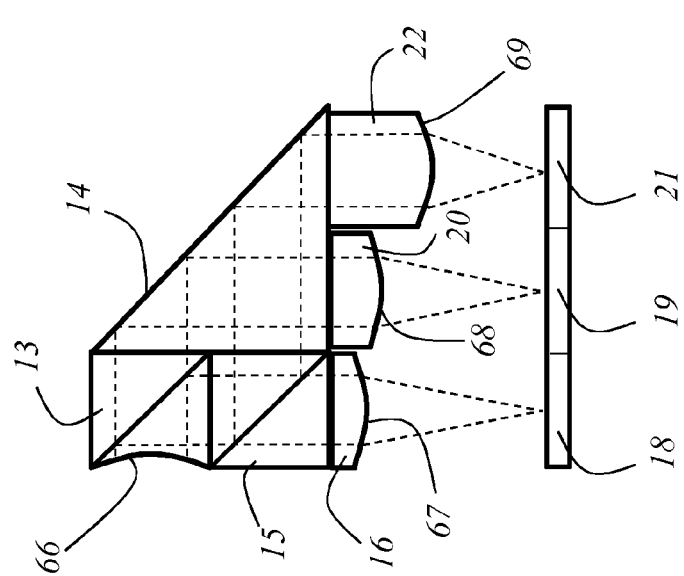
FIG. 14 is a detailed view of a tenth embodiment, with curved interfaces.
Figure 15B:
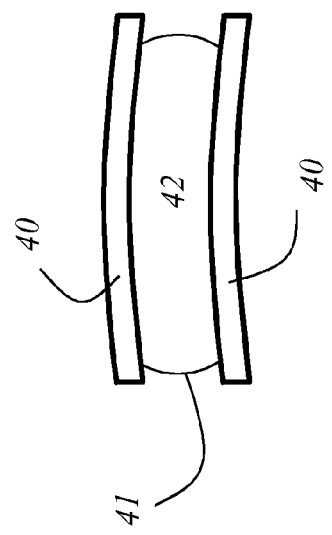
FIGS. 15a and 15b show an embodiment of an adjustable optical component with curved interfaces.
Figure 15A:
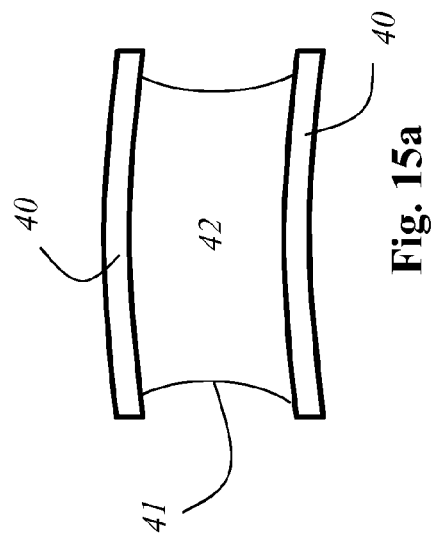

FIG. 14 is a detailed view of a tenth embodiment, in which the first interface 66 of the first beam splitter 13, which the detection light 11 encounters, is curved in a convex manner, while the last interface 67, 68, 69 respectively for the individual detection beam path branches is curved in a concave manner. The embodiment otherwise corresponds substantially to the embodiment shown in FIG. 1.

A particular additional axial offset of the focus of the detection light 11 can be achieved even in the case of an adjustable optical component. This is also without differently than in the case of a lens the convergence angle ß of the respective detection light beam focused on a surface detector element changing. The embodiment shown in FIGS. 15a and 15b substantially corresponds to the embodiment shown in FIGS. 9a and 9b, wherein however the limiting discs 40 are not flat for said purpose, but are executed curved (both with the same radius of curvature).

Figure 16B:
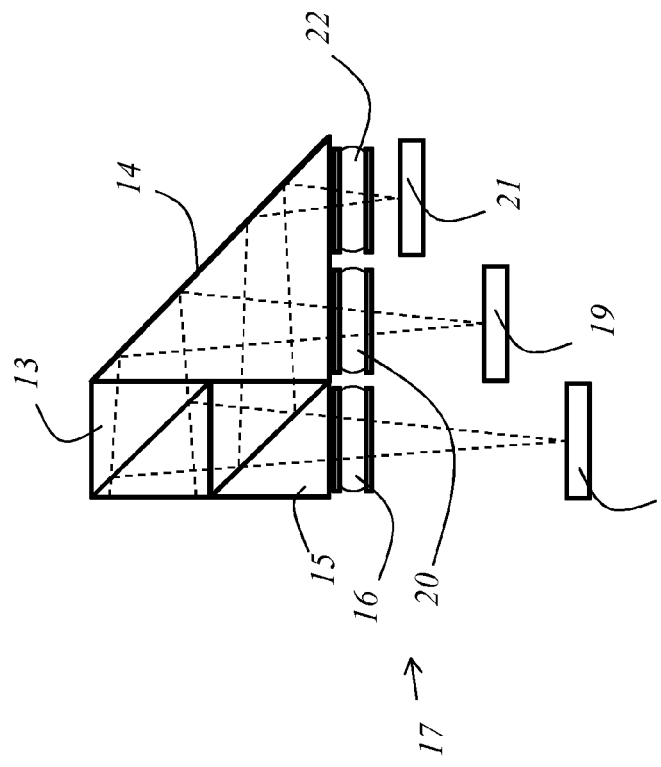
FIGS. 16a and 16b show an eleventh embodiment of a device according to the invention with direct placing of the detectors in the focus planes.
Figure 16A:
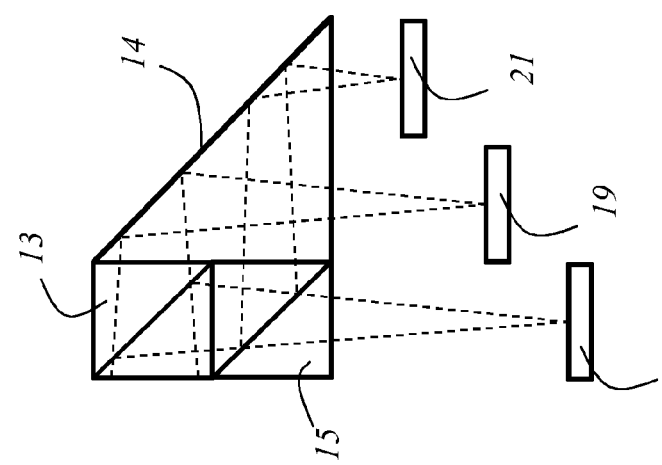

FIG. 16a shows an eleventh embodiment, in which the three surface detector elements 18, 19, 21 can be displaced along their optical axis standing perpendicular in such a way that the three surface detector elements each lie in the optimal focus position. In this case, the three surface detector elements could either be fixedly anchored in their respective focus position or held movably in the sense that their position along the optical axis can be adjusted, for example, by a mechanical, pneumatic or electrical drive, or by a drive based on the piezoelectric effect, in order to reach a certain position on the optical axis. In the arrangement shown in FIG. 16b, the arrangement from FIG. 16a was expanded equivalent to the previous embodiments by three optical components 16, 20, 22, which are part of an adjusting device 17 for adjusting the optical path lengths of the detection beam path branches, in such a way that in front of each surface detector element an optical component is arranged for the purpose of fine adjustment of the focus position on the respectively associated surface detector element. This can be achieved according to the invention in any of the ways previously described above, for example by using suitable glass blocks and/or by using an optical component 16, 20, 22 of variable thickness.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for single plane illumination microscopy (SPIM) analysis of a sample, the method comprising:
   simultaneously illuminating multiple sample layers by a single sheet of light; and
   detecting detection light emanating from the individual sample layers at different times and/or at different positions in a detection beam path, wherein the detection beam path is branched using beam splitters and wherein an effective refractive power of the individual beam splitters is zero.

2. The method according to claim 1, wherein:
   a. the detection light emanating from the different sample layers is focused spatially separately and simultaneously onto separate surface detector elements, and/or
   b. the detection light of the different sample layers is detected simultaneously by a plurality of separate surface detector elements.

3. The method according to claim 2, wherein the detection beam has a plurality of detection beam path branches each having at least one surface detector element.

4. The method according to claim 3, wherein optical path lengths of the detection beam path branches for imaging the sample layers onto the surface detector elements are adjustable in that the surface detector elements are moveable along their optical axis.

5. The method according to claim 3, wherein optical path lengths of the detection beam path branches for imaging the sample layers onto the surface detector elements are adjusted by an adjusting device in such a way that the detection light emanating from a sample layer is focused onto a first surface detector element of a first detection beam path branch, and wherein the detection light emanating from another sample layer is focused onto a second surface detector element of a second detection beam path branch.

6. The method according to claim 5, wherein:
   a. the optical path length of a first detection beam path branch and the optical path length of a second detection beam path branch are adjusted and/or are adjustable independently of one another,
   b. the adjusting device comprises a plurality of adjusting elements and each detection beam path branch has its own adjusting element, with which the optical path length of the respective detection beam path branch is adjusted and/or is adjustable,
   c. the adjusting device has at least one adjusting element, with which the optical path lengths of at least two detection beam path branches are varied and/or are variable at the same time, and/or
   d. the optical path lengths of a first detection beam path branch and the optical path lengths of a second detection beam path branch are different.

7. The method according to claim 1, wherein the detection light emanating from the different sample layers is focused in temporal succession onto the same surface detector element.

8. The method according to claim 7, wherein:
   a. the detection light emanating from one of the sample layers and passing through a detection lens is guided on a detection beam path, the optical path length of which is adjusted by an adjusting device in such a way that the detection light emanating from the one of the sample layers is focused onto the surface detector element, wherein the surface detector element, to obtain image data of this sample layer, is read at a setting of the adjusted path length, and then
   b. the optical path length of the detection beam path is adjusted by the adjusting device in such a way that the detection light emanating from another of the sample layers is focused onto the surface detector element, wherein the surface detector element, to obtain image data of the other sample layer, is read afresh at another setting of the optical path length.

9. The method according to claim 1, wherein:
   a. the sample layers are aligned parallel to one another,
   b. a stack of a multiplicity of sample layers aligned parallel to one another are illuminated and imaged simultaneously or sequentially,
   c. the sample layers are oriented perpendicular to an optical axis of a detection lens,
   d. the sample layers are spaced apart from one another, and/or
   e. the sample layers are spaced apart from one another and have a spacing from one another that is greater than an optical resolution of a detection arrangement used.

10. The method according to claim 1, wherein:
    a. the sheet of light is formed as a quasi light sheet, which is generated by waving an illumination light beam back and forth,
    b. the light sheet plane is oriented perpendicular to an optical axis of a detection lens,
    c. the sheet of light is directed in such a way that it encounters the sample and/or runs through the sample at an angle different from zero degrees to the optical axis of the detection lens,
    d. the sheet of light is directed in such a way that it encounters the sample and/or runs through the sample perpendicular to the optical axis of the detection lens, and/or
    e. the sheet of light has an extension in the direction of the optical axis of the detection lens that is greater than a field depth range of a detection arrangement, which comprises the detection lens and the detection beam path.

11. The method tithed according to claim 1, wherein, following a detection of the detection light emanating from the multiple sample layers, further multiple sample layers are illuminated and the detection light emanating from the further sample layers is detected.

12. The method according to claim 1, wherein:
    a. image data is produced simultaneously or sequentially with regard to the multiple sample layers and/or further multiple sample layers, wherein the sample always remains stationary,
    b. image data is produced simultaneously or sequentially with regard to the multiple sample layers and/or further multiple sample layers, wherein the sample and a detection lens always remain stationary,
    c. image data is produced simultaneously or sequentially with regard to the multiple sample layers and/or further multiple sample layers, wherein the sample, the detection lens and the surface detector element, in particular all the surface detector elements, always remain stationary,
    d. the sample remains stationary during an adjustment of an adjusting device, e. the sample and the detection lens remain stationary during the adjustment of the adjusting device,
f. the sample, the detection lens and the surface detector element, in particular all the surface detector elements, remain stationary during the adjustment of the adjusting device,
g. the geometrical path length of at least one detection beam path branch remains constant during the adjustment of the optical path length of the detection beam path branch, and/or
h. the geometrical path length of the detection beam path remains constant during the adjustment of the optical path length of the detection beam path.

13. The method according to claim 2, wherein:
a. the surface detector elements are parts of the same surface detector, or that
b. the surface detector elements are separate surface detectors or at least parts of surface detectors that are separate from one another.

14. The method according to claim 1, wherein the method is carried out using a scanning microscope and/or a confocal scanning microscope.

15. A device configured to perform the method according to claim 1.

16. A device for single plane illumination microscopy (SPIM) analysis of a sample, the device comprising:
an illuminator configured to generate a sheet of light; and
a detection arrangement comprising a detection lens and a detection beam path, wherein the illuminator is configured to illuminate multiple sample layers of a sample to be analyzed simultaneously with the sheet of light and the detection arrangement is configured to detect detection light emanating from the individual sample layers in the detection beam path at different times and/or at different positions, wherein the detection beam path is branched using beam splitters and wherein an effective refractive power of the individual beam splitters is zero.

17. The device according to claim 15, wherein:
a. the detection light emanating from different sample layers is focused spatially separated and simultaneously onto different surface detectors, and/or
b. the detection arrangement detects the detection light of a plurality of different sample layers simultaneously with a plurality of different surface detectors.

18. The device according to claim 15, wherein:
a. the detection beam path is branched and has a plurality of detection beam path branches each having at least one surface detector, and/or
b. for the simultaneous imaging of multiple sample layers, the optical path lengths of the detection beam path branches are adjustable in such a way that the detection light emanating from a sample layer is focused onto a first surface detector of a first detection beam path branch and that the detection light emanating from another sample layer is focused onto a second surface detector of a second detection beam path branch.

19. The device according to claim 15, further comprising an adjuster configured to adjust the optical path length of the detection beam path or at least of one of the detection beam path branches.

20. The device according to claim 18, wherein:
a. the optical path lengths of a first detection beam path branch and the optical path lengths of a second detection beam path branch are adjustable independently of one another,
b. the adjuster comprises a plurality of adjusting elements and each detection beam path branch has its own adjusting element, with which the optical path length of the detection beam path branch is adjusted and/or is adjustable,
c. the adjuster has at least one adjusting element, with which the optical path lengths of at least two detection beam path branches are variable at the same time, and/or
d. the optical path lengths of a first detection beam path branch and the optical path lengths of a second beam path branch are different.

21. The device according to claim 15, further comprising an adjuster configured to optionally adjust an optical path length of the detection beam path from the detection lens to a surface detector in such a way that either the detection light emanating from a first of the sample layers or the detection light emanating from a second of the sample layers is focused onto the surface detector.

22. The device according to claim 19, wherein
a. image data is generatable simultaneously or sequentially with regard to the multiple sample layers and/or further multiple sample layers, wherein the sample always remains stationary,
b. image data is generatable simultaneously or sequentially with regard to the multiple sample layers and/or further multiple sample layers, wherein the sample and the detection lens always remain stationary,
c. image data is generatable simultaneously or sequentially with regard to the multiple sample layers and/or further multiple sample layers, wherein the sample, the detection lens and all the surface detectors, always remain stationary,
d. the adjuster is formed and arranged in such a way that the sample, the detection lens and/or all the surface detectors remain stationary during the adjustment of the optical path length, and/or
e. the adjuster is formed and arranged in such a way that the geometrical path length of the detection beam path and/or of at least one detection beam path branch remains constant during the adjustment of the optical path length.

23. The device according to claim 19, wherein:
a. the adjuster or an adjusting element of the adjuster has a plurality of different transparent optical components, which are insertable in exchange for one another into the detection beam path and/or into a detection beam path branch,
b. the adjuster or an adjusting element of the adjuster has a plurality of transparent optical components, which are insertable independently of one another into the detection beam path and/or into a detection beam path branch,
c. the adjuster or an adjusting element of the adjuster has a plurality of transparent optical components arranged on a turret or on a displacement arrangement,
d. the adjuster or an adjusting element of the adjuster has at least one transparent block, which is arranged rotatably and/or displaceably in such a way that a proportion of the block located in the detection beam path and/or in a detection beam path branch is variable,
e. the adjuster or an adjusting element of the adjuster has at least one transparent optical component that is formed as a solid block, and/or f. the adjuster or an adjusting element of the adjuster has at least one transparent optical component having two interfaces curved in the same direction and/or with the same radius of curvature.

24. The device according to claim 19, wherein:
a. the adjuster or an adjusting element of the adjuster has at least one optical component that is adjustable in geometrical and/or optical thickness,
b. the adjuster or an adjusting element of the adjuster has at least one optical component that is variable in shape,
c. the adjuster or an adjusting element of the adjuster has at least one vessel that is variable in shape and is filled with a fluid,
d. the adjuster or an adjusting element of the adjuster has at least one adjustable optical component having two transparent limiting discs, the spacing of which is adjustable and between which a liquid optical medium is arranged,
e. the adjuster or an adjusting element of the adjuster has at least one adjustable optical component having two transparent limiting discs that are curved in the same direction and/or with the same radius of curvature, the spacing of which is adjustable and between which a liquid optical medium is arranged, and/or
f. the adjuster or an adjusting element of the adjuster has at least one adjustable optical component having two transparent limiting discs, the spacing of which is adjustable and between which a liquid optical medium is arranged, wherein a resilient film together with the limiting discs encloses a receiving space for the optical medium.

25. The device according to claim 15, wherein:
a. the sheet of light is formed as a quasi light sheet, which is produced by waving an illumination light beam, which is round in cross section, back and forth,
b. the light sheet plane is oriented perpendicular to the optical axis of the detection lens,
c. the sheet of light is directed in such a way that the sheet of light encounters the sample at an angle different from zero degrees to the optical axis of the detection lens, and/or that
d. the sheet of light is directed in such a way that the sheet of light encounters the sample perpendicular to the optical axis of the detection lens, and/or
e. the sheet of light has an extension in a direction of the optical axis of the detection lens that is greater than a field depth range of the detection arrangement, which comprises the detection lens and the detection beam path.

26. The device according to claim 17, wherein
a. the surface detectors are parts of the same surface detector, or
b. the surface detectors are parts of surface detectors that are separate from one another.

27. The device according to claim 15, wherein the device includes a scanning microscope and/or a confocal scanning microscope and/or is formed from a scanning microscope and/or a confocal scanning microscope.

* * * * *